United States Patent
Liu et al.

(10) Patent No.: US 10,478,137 B2
(45) Date of Patent: Nov. 19, 2019

(54) MULTIPLE IMAGING MODALITY IMAGING APPARATUS

(71) Applicant: KONINKLIJKE PHILIPS N.V., Eindhoven (NL)

(72) Inventors: Jinling Liu, Solon, OH (US); Steven John Plummer, Hudson, OH (US); Dawn Barile, Highland Heights, OH (US); Krassimir Todorov Krastev, Eindhoven (NL); Johannes Balthasar Maria Soetens, Esbeek (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 1361 days.

(21) Appl. No.: 14/390,530

(22) PCT Filed: Apr. 8, 2013

(86) PCT No.: PCT/IB2013/052791
§ 371 (c)(1),
(2) Date: Oct. 3, 2014

(87) PCT Pub. No.: WO2013/160781
PCT Pub. Date: Oct. 31, 2013

(65) Prior Publication Data
US 2015/0092906 A1    Apr. 2, 2015

Related U.S. Application Data

(60) Provisional application No. 61/636,761, filed on Apr. 23, 2012.

(51) Int. Cl.
*A61B 6/00* (2006.01)
*A61B 6/03* (2006.01)
(Continued)

(52) U.S. Cl.
CPC .......... *A61B 6/4417* (2013.01); *A61B 5/0035* (2013.01); *A61B 5/055* (2013.01);
(Continued)

(58) Field of Classification Search
CPC ....... A61B 5/0035; A61B 5/055; A61B 6/032; A61B 6/035; A61B 6/037; A61B 6/0407;
(Continued)

(56) References Cited

U.S. PATENT DOCUMENTS 8,452,381 B2    5/2013    Cora
9,029,787 B2    5/2015    Yamaya
(Continued)

FOREIGN PATENT DOCUMENTS

JP    2006212443    8/2006
JP    2001202976    8/2007
(Continued)

OTHER PUBLICATIONS

Kemp, B. J., et al.; NEMA NU Feb. 2007 performance measurements of the Siemens Inveon TM preclinical small animal PER system; 2009; Phys. Med. Biol.; 54:2359-2376.
(Continued)

*Primary Examiner* — Mark D Remaly

(57) ABSTRACT

An imaging apparatus includes a first imaging modality ($102_1$), a second imaging modality ($102_2$), wherein the first and second imaging modalities are in alignment with scanning zones for scanning an object or subject, and a third imaging modality ($102_N$) which is selectively moveable between a first location (114) in which the third imaging modality is in alignment with the scanning zones for scanning the object or subject and a second location (122) in which the third imaging modality is outside of alignment with the scanning zones.

15 Claims, 10 Drawing Sheets

(51) Int. Cl.
*A61B 5/00* (2006.01)
*A61B 5/055* (2006.01)
*A61B 8/13* (2006.01)
*A61B 8/00* (2006.01)
*A61B 6/04* (2006.01)

(52) U.S. Cl.
CPC .............. *A61B 6/032* (2013.01); *A61B 6/035* (2013.01); *A61B 6/037* (2013.01); *A61B 6/5235* (2013.01); *A61B 8/13* (2013.01); *A61B 8/4416* (2013.01); *A61B 6/0407* (2013.01)

(58) Field of Classification Search
CPC ....... A61B 6/4417; A61B 6/5235; A61B 8/13; A61B 8/4416
See application file for complete search history.

(56) References Cited

U.S. PATENT DOCUMENTS

| | | |
|---|---|---|
| 2007/0238950 A1 | 10/2007 | Vija et al. |
| 2008/0081985 A1 | 4/2008 | Zheng |
| 2009/0159805 A1 | 6/2009 | Feke |

FOREIGN PATENT DOCUMENTS

| | | |
|---|---|---|
| JP | 2010223956 | 10/2010 |
| WO | 2012/049590 | 4/2012 |

OTHER PUBLICATIONS

Siemens; Inveon Product Brochure; 2008; http://www.medical.siemens.com/siemens/en_GB/gg_nm_FBAs/files/broch/br_09_inveon.pdf.

MULTIPLE IMAGING MODALITY IMAGING APPARATUS

The following generally relates to an imaging apparatus and more particularly to an imaging apparatus that includes at least two moveable imaging modalities (e.g., scanners) that alternatively share a same examination zone.

A hybrid imaging system such as positron emission tomography/computed tomography (PET/CT) imaging system has included a single patient support and two different imaging modalities, e.g., one for acquiring functional data and the other for acquiring structural data. In one configuration, the single patient support is moveable and is moved between the two stationary modalities of the hybrid system. By way of example, the single patient support is first used in connection with the first modality to position a patient for scanning with the first modality.

Then, the subject support is physically moved to the second modality of the hybrid system for scanning the patient with the second modality. Unfortunately, moving the patient support between the two different modalities may result in movement of patient on the patient support and/or anatomical organs of the patient, which may degrade alignment or registration of the data sets of the different modalities, and consumes time that could otherwise be used for scanning and/or communicating with patients.

In another configuration, the two imaging modalities are stationary and aligned with respect to each other along the long axis of the single patient support and a scan axis. In this configuration, the single patient support is also stationary and alternatively feeds and positions the patient thereon in the examination region of the first modality for a scan with that modality or in the examination region of the second modality for a scan with that modality by selectively extending the tabletop of the patient support. However, if the patient is scheduled for a third procedure with an imaging modality located in another examination room, the patient will have to be transported to the other examination room.

As discussed above, moving the patient support between modalities may cause patient motion and negatively affect dataset alignment and registration. Where the third imaging modality uses a same administered imaging agent as one of the imaging modalities of the hybrid system, the time consumed to move the patient to the other imaging modality may result in additional agent administration to the patient due to isotope decay.

Alpha or other testing of an imaging modality under development in the clinical setting has resulted in tying up an examination room at an imaging facility where the prototype or test system occupies an examination room, and prohibits installing of a diagnostic system in the same examination room. This may not be feasible in some imaging centers due to a limited number of examination rooms and/or examination room space, and/or patient throughput demands. In research work, there currently is no good way to compare like modalities, except to scan on different systems, in different rooms, etc. In addition, upgrades can be an issue as new systems would need to be purchased and/or systems would have to be reconfigured.

Alternatively, an imaging modality under development, in research, etc. could be physically integrated with an existing imaging system in an examination room, for example, as a hybrid system with multiple modalities. For example, one of the two modalities of the hybrid system could be replaced with the imaging modality under development. Unfortunately, this generally requires structural and electrical modifications to the imaging system, and the modified system may be unsuitable or unusable for reimbursable diagnostic scans, thereby limiting its functionality. This may dissuade imaging centers from participating in alpha testing, adding development cost and time, and extending time to market with newer imaging technologies.

Aspects described herein address the above-referenced problems and/or others.

In one aspect, an imaging apparatus includes a first imaging modality, a second imaging modality, wherein the first and second imaging modalities are in alignment with scanning zones for scanning an object or subject, and a third imaging modality which is selectively moveable between a first location in which the third imaging modality is in alignment with the scanning zones for scanning the object or subject and a second location in which the third imaging modality is outside of alignment with the scanning zones.

In another aspect, an imaging apparatus includes first imaging modality that moves between a scanning position and a first non-scanning position and second different imaging modality that moves between the scanning position and a second non-scanning position, wherein the first and the second imaging modalities alternatively move to the scanning position to scan a subject or object.

In another aspect, an imaging apparatus includes a first imaging modality stationarily affixed at a first scanning position and a second imaging modality moveable into and out of a second scanning position, wherein the second imaging modality is pre-aligned with the second scanning position such that moving the second imaging modality to the second scanning position automatically aligns the second imaging modality with the second scanning position to scan a subject or object.

In another aspect, a method includes moving a first imaging modality alternately between a first location in which the first imaging modality is in alignment with scanning zones of second and third imaging modalities and a second location in which the first imaging modality is outside of alignment with the scanning zones.

In another aspect, a method includes alternatively positioning first and second imaging modalities at a scanning position to scan a subject or object, wherein the first imaging modality moves between the scanning position and a first non-scanning position and the second different imaging modality moves between the scanning position and a second non-scanning position.

In another aspect, a method includes alternatively positioning a moveable imaging modality between scanning and non-scanning positions, wherein the moveable imaging modality is pre-aligned with the scanning position and a scanning position of a stationarily affixed imaging modality.

The invention may take form in various components and arrangements of components, and in various steps and arrangements of steps. The drawings are only for purposes of illustrating the preferred embodiments and are not to be construed as limiting the invention.

FIG. 1 schematically illustrates a top down view of an example imaging apparatus that includes at least a plurality of moveable imaging modalities combined to form the imaging apparatus.

FIG. 2 schematically illustrates the example imaging apparatus of FIG. 1 with one of the moveable imaging modalities positioned in a shared examination zone.

FIG. 3 schematically illustrates the example imaging apparatus of FIG. 1 with another one of the moveable imaging modalities positioned in a shared examination zone.

Figure 8:
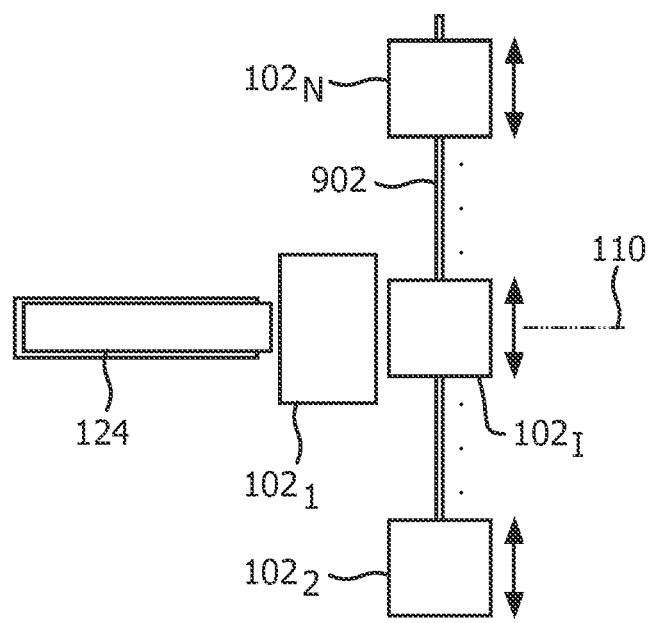

FIG. 8 schematically illustrates a variation in which a plurality of moveable imaging modalities translates to the examination zone along an axis transverse to the scan axis.

Figure 9:
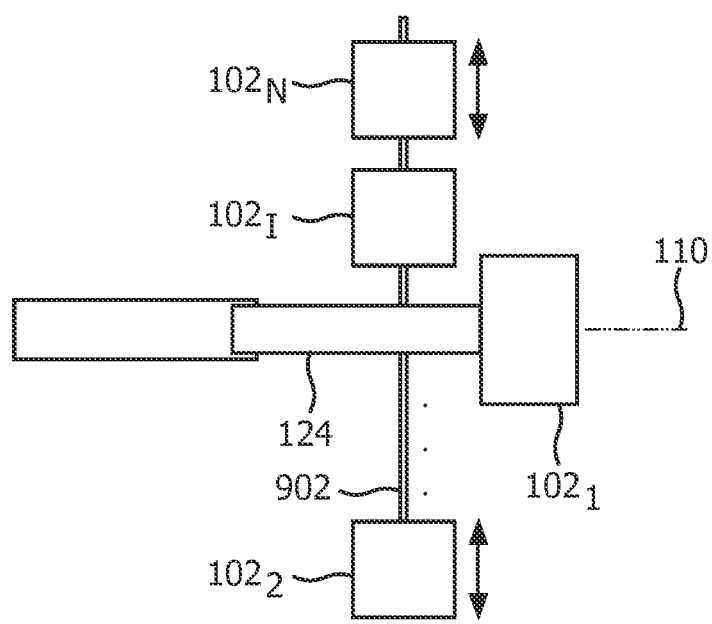

FIG. 9 schematically illustrates a variation in which a plurality of moveable imaging modalities that translate to the examination zone along an axis transverse to the scan axis are located between the subject support and a stationary imaging modality.

Figure 10:
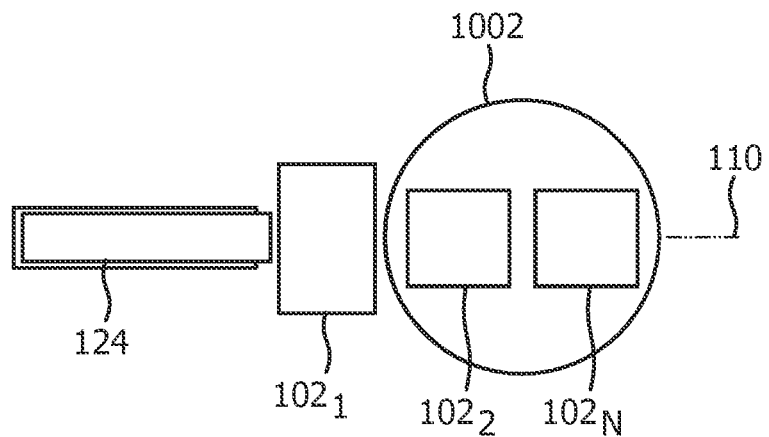

FIG. 10 schematically illustrates a variation in which a plurality of moveable imaging modalities are aligned along the scan axis and rotate to position an imaging modality at the examination zone.

Figure 11:
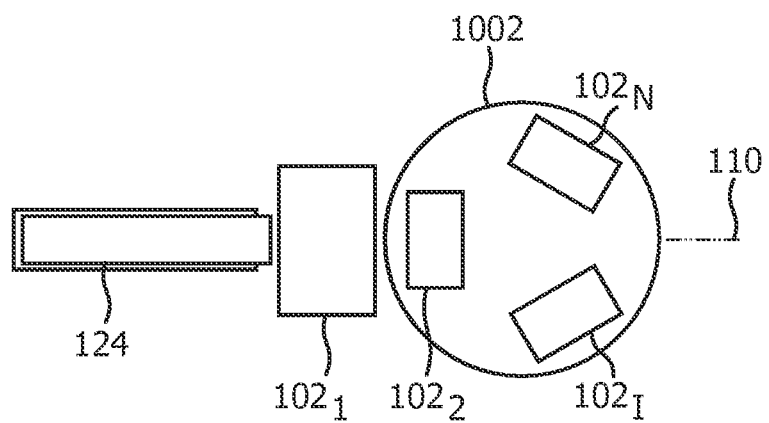

FIG. 11 schematically illustrates a variation in which a plurality of moveable imaging modalities are arranged angularly offset from each other and rotate to position an imaging modality at the examination zone.

Figure 12:
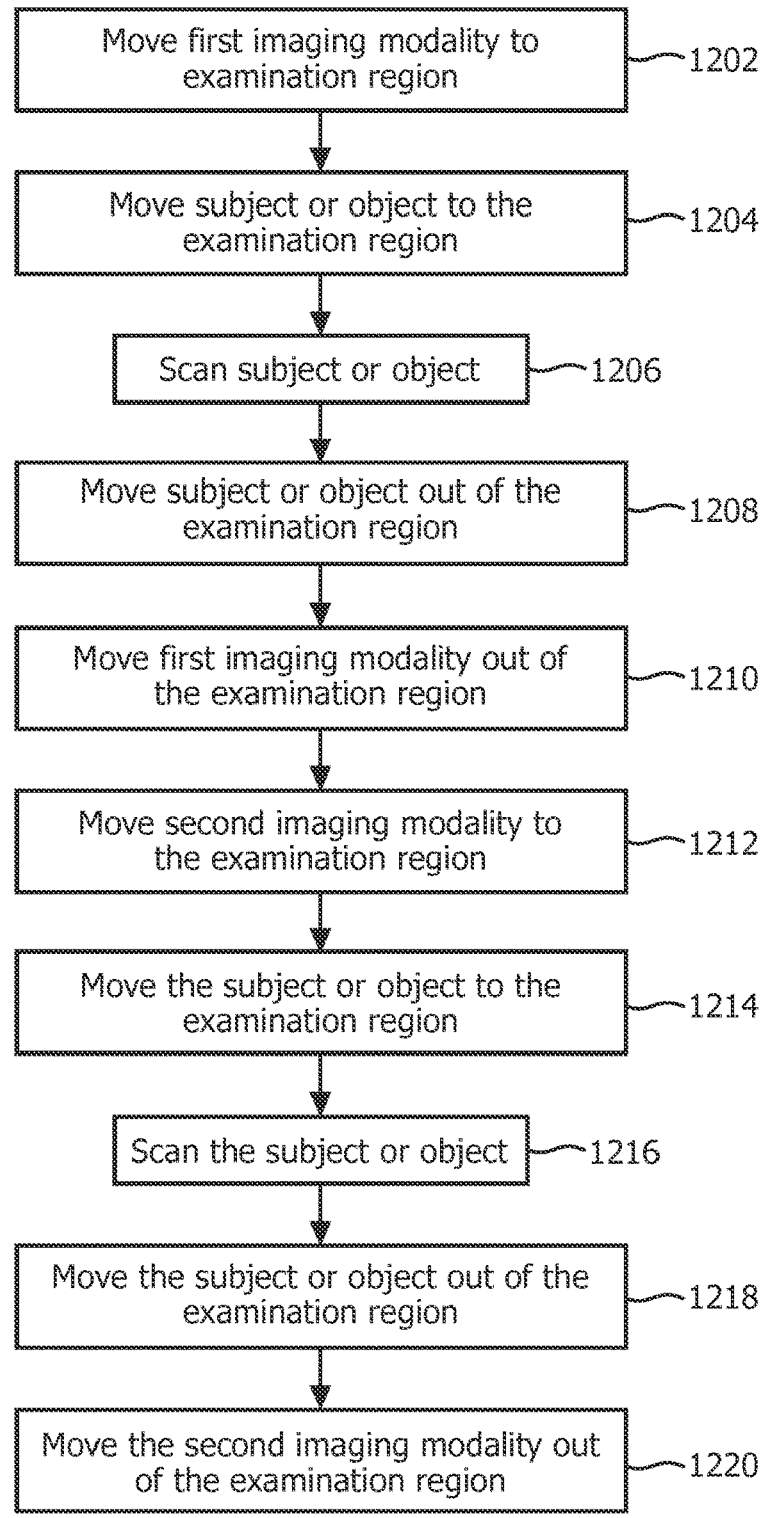

FIG. 12 illustrates an example method.

Figure 13:
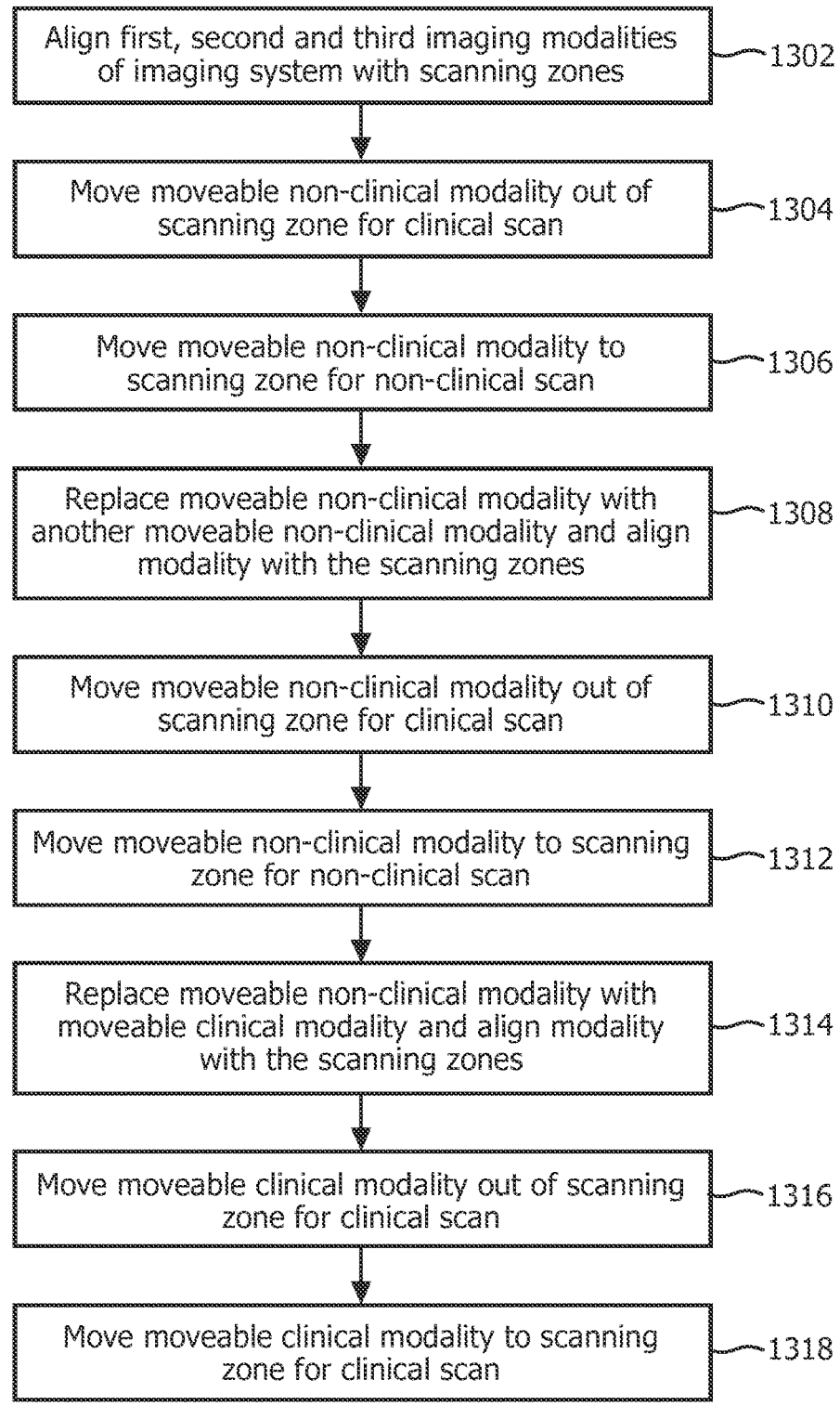

FIG. 13 illustrates another example method.

Figure 1:
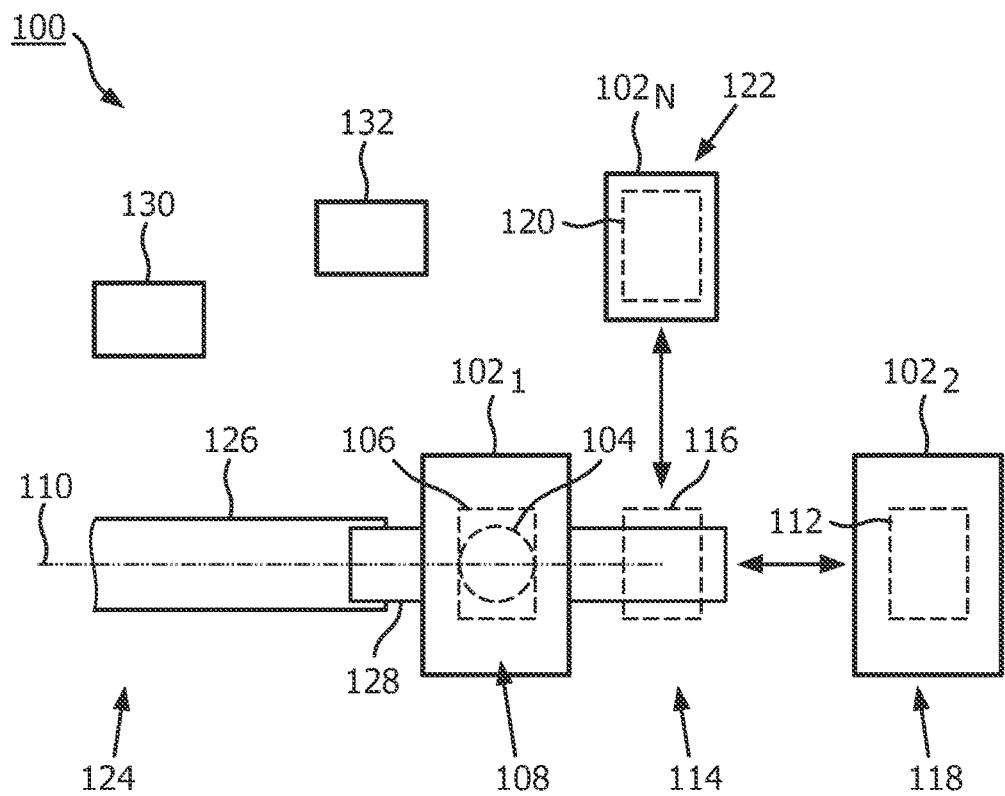

Initially referring to FIG. 1, a top down view of an example imaging apparatus 100 that includes a plurality (e.g., two, three, four, etc.) of imaging modalities combined to form the imaging apparatus 100 is schematically illustrated. For sake of clarity, only three imaging modalities—a first imaging modality $102_1$, a second imaging modality $102_2$, and a third imaging modality $102_N$ (collectively referred to as imaging modalities 102)—are shown. Note that the terms "first," "second," "third," . . . merely correspond to the order in which elements (e.g., the imaging modalities) are introduced.

Suitable imaging modalities include, but are not limited to computed tomography (CT), positron emission tomography (PET), magnetic resonance imaging (MRI), single photon emission tomography (SPECT), and ultrasound (US). In one instance, each of the plurality of imaging modalities of the apparatus 100 is a different modality (e.g., CT, SPECT and PET, etc.). In another instance, at least two of the plurality of imaging modalities of the apparatus 100 are different configurations of a same imaging modality (e.g., analog PET and digital (solid state) PET, etc.).

In the illustrated embodiment, the first imaging modality $102_1$ is stationary and includes a first scan field of view 104 that is aligned with a first examination zone 106, which is located at a first location 108 along a scan axis 110. The first imaging modality $102_1$ is a whole or full body or other scanner. The second imaging modality $102_2$ includes a second scan field of view 112 and is configured to translate in a direction of the scan axis 110 between at least a second location 114 at which the second scan field of view 112 aligns with a second examination zone 116 and a home or park location 118 at which the second imaging modality $102_2$ is outside of the second examination zone 116. The second imaging modality $102_2$ is also a whole or full body or other scanner.

The third imaging modality $102_N$ includes a third scan field of view 120 and is configured to translate in a direction transverse (approximately perpendicular) to the scan axis 110 between the at least second location 114 at which the third scan field of view 120 aligns with the second examination zone 116 and a home or park location 122 at which the third imaging modality $102_N$ is outside of the second examination zone 116. The third imaging modality $102_N$ is a whole or full body or other scanner. In the illustrated embodiment, the second and third imaging modalities $102_2$ and $102_N$ are both spatially registered with the same examination zone—the second examination zone 116, and, thus, the second and third field of views 112 and 120 are spatially registered with each other.

As described in greater detail below, the second imaging modality $102_2$ and the third modality $102_N$ are alternatively positioned at the second location 114 for scanning purposes. (FIG. 1 shows both the second imaging modality $102_2$ and the third modality $102_N$ at their respective home or parked locations 118 and 122.) Alternatively positioning the second imaging modality $102_2$ and the third modality $102_N$ in connection with the second examination zone 116 can be done as part of a single imaging examination that only involves one of the second or third imaging modalities $102_2$ and $102_N$, one of the second or third imaging modalities $102_2$ and $102_N$ and the first imaging modality $102_1$, all three of the imaging modalities $102_1$, $102_2$, and $102_N$, etc.

A subject support 124 is common to and shared by the imaging modalities $102_1$, $102_2$, . . . , $102_N$ and supports a subject or object before, during and/or after scanning in the examination zones 106 and 116. The subject support 124 includes a stationarily mounted base 126 and a tabletop 128, which is slideably affixed to the base 126 and configured to move a subject or object on the tabletop 128 between at least the first location 108 and the second location 114 (and, optionally, one or more other locations such as a subject load, subject unload, subject support park, etc. location). The tabletop 128 is shown extending to second examination zone 116 at the second location 114.

An operator console 130 allows a user to control the imaging apparatus 100, including selecting an imaging protocol, moving the subject support 124, initiating scanning via one or more of the imaging modalities $102_1$, $102_2$, . . . , $102_N$, etc. In a variation, one or more of the imaging modalities $102_1$, $102_2$, . . . , $102_N$ is alternatively operated by a different computer. For example, in another embodiment, the third (or other) imaging modality $102_N$ is controlled by an optional second operator console 132 and not the console 130. As described herein, the optional second operator console 132 can control the third imaging modality $102_N$ to scan a patient even where the console 130 controls the subject support 124 to position a subject or object at the second examination zone 116.

Generally, the operator console 130 and/or the optional second operator console 132 include a computer with one or more processors for executing computer readable instructions encoded on computer readable storage medium such as physical memory or other non-transitory medium. Alternatively or additionally, the one or more processors can execute computer readable instructions carried by a carrier wave, signal, or other transitory medium. The operator console 130 and/or the optional second operator console 132 also include an output device such as a monitor or display and an input device such as a keyboard and/or a mouse.

Note that the relative size and/or shape of the components and/or features 102-128 with respect to each other are for explanatory purposes and are not limiting.

It is to be appreciated that the third (or other) imaging modality $102_N$ can be removably incorporated with the apparatus 100. For example, the apparatus 100 may initially only include the first and second imaging modalities $102_1$ and $102_2$, with the third imaging modality $102_N$ later incorporated into the apparatus 100. In one instance, the third modality $102_N$ may include a prototype scanner under development and entering beta or other testing. As such, the third imaging modality $102_N$ can be added to the apparatus 100 for testing and then removed afterwards, where the apparatus 100 can be utilized as it was before the integration with the third imaging modality $102_N$ incorporated therein and after the third imaging modality $102_N$ is removed.

In one instance, this allows for temporary testing of the third modality $102_N$ in the clinical setting without tying up an examination room and can save development time and cost by leveraging the existing apparatus 100, for example, the subject support 124, etc. Where the third imaging modality $102_N$ is temporarily added, e.g., for testing, the third imaging modality $102_N$ can be incorporated into the apparatus 100 without any structural modification to the apparatus 100. For example, in one instance, a geometry of the third imaging modality $102_N$ is such that it can fit between the first imaging modality $102_1$ and the second imaging modality $102_2$ when the second imaging modality $102_2$ is at the second location 118. In this instance, the third imaging modality $102_N$ can be added without mechanical and/or electrical modification to the apparatus 100.

Furthermore, a separate console (e.g., the console 132, which is separate from the console 130) can be used to control the third imaging modality $102_N$ so the temporarily added third imaging modality $102_N$ can be incorporated into the apparatus 100 without any software changes to the console 130. In this instance, the console 130 would still control the subject support 124, but the console 132 for the third imaging modality $102_N$ would control data acquisition and post-processing. With this instance, the third modality $102_N$ can be pre-calibrated with the second examination zone 116, e.g., via registration with the first and/or the second imaging modalities $102_1$ and $102_2$ so that the support 124 can be operated from the console 130 in coordination with scanning with the third modality $102_N$.

In another instance, after testing, the third modality $102_N$ can remain part of the apparatus 100, for example, as a diagnostic scanner of the apparatus 100. In another instance, the third modality $102_N$ is a purchasable option. In this instance, the third modality $102_N$ can be purchased up front and installed and incorporated with the apparatus 100. Alternatively, the third modality $102_N$ can be later purchased and added to the apparatus 100, using the console 130 and/or the console 132 to control the third modality $102_N$. In yet another instance, the third modality $102_N$ may be a scanner that is used infrequently and is combined with the first and second imaging modalities $102_1$ and $102_2$. One or more of the above allows for sharing a single examination room with multiple modalities rather than occupying separate examination rooms for each modality.

Figure 2:
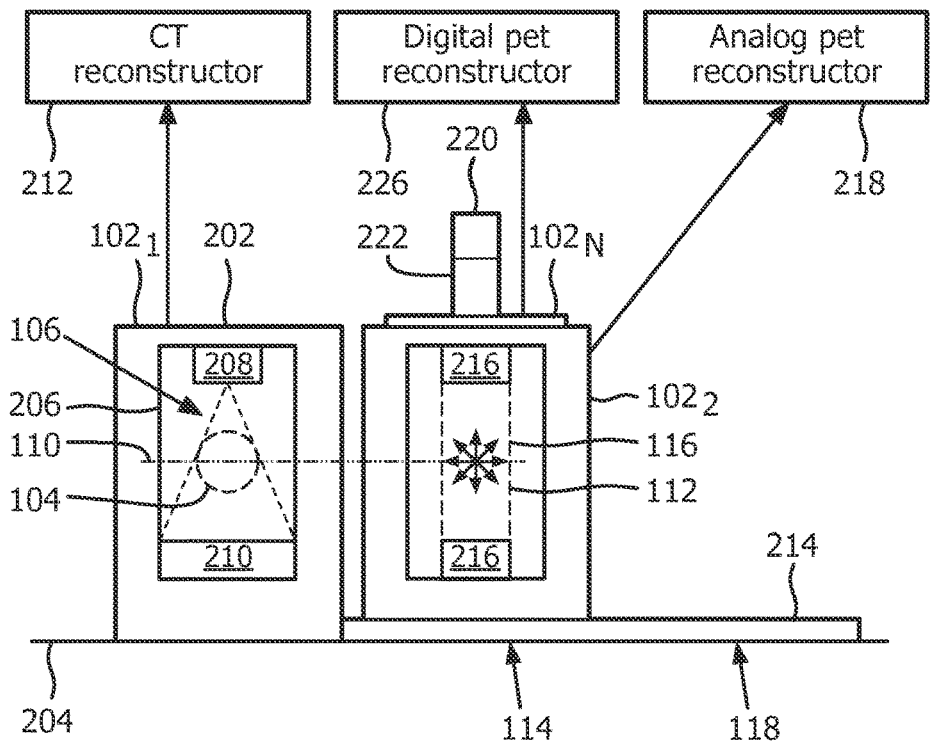
Figure 3:
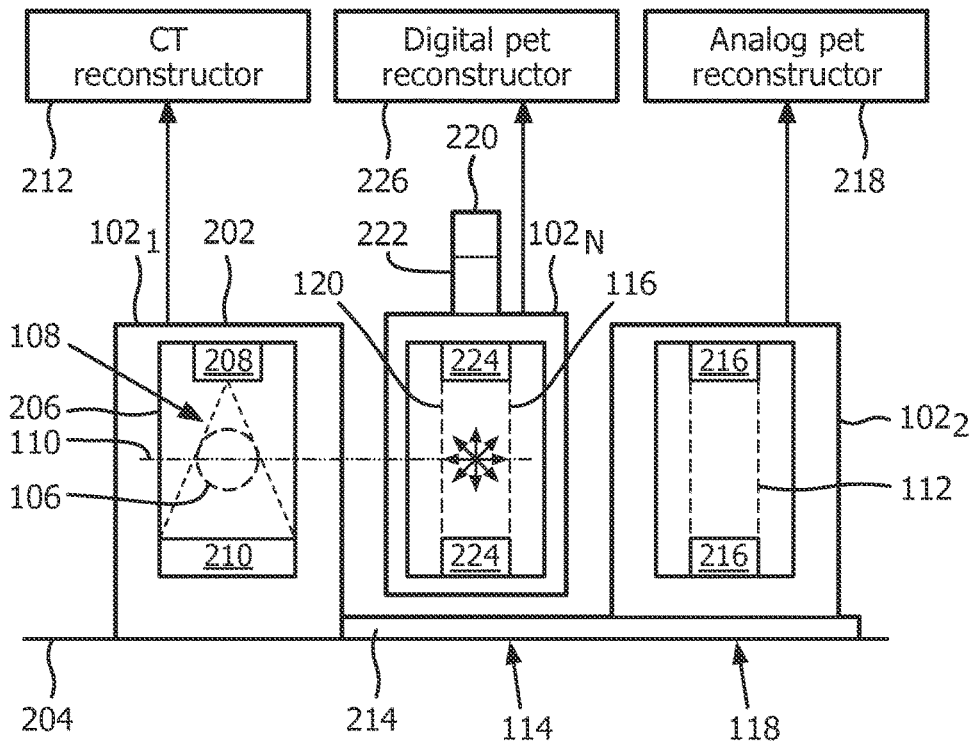

FIGS. 2 and 3 schematically illustrate a side view of the apparatus 100 in which the first modality $102_1$ is a CT scanner, the second modality $102_2$ is an analog PET scanner, and the third modality $102_N$ is a solid-state (digital) PET scanner. FIG. 2 shows a configuration in which the second modality $102_2$ is at the second location 114 in the second examination zone 116, and FIG. 3 shows a configuration in which the third modality $102_N$ is at the second location 114 in the second examination zone 116.

With reference to FIGS. 2 and 3, the first modality $102_1$ includes a stationary gantry portion 202, which, in this example, is affixed to an examination room floor 204, and a rotating gantry portion 206, which is rotatably supported by the stationary gantry portion 202 and rotates about the scan axis 110. A radiation source 208, such as an x-ray tube, is supported by the rotating gantry portion 206 and rotates therewith. The radiation source 208 emits radiation that traverses the first field of view 104 and the first examination zone 106. A radiation sensitive detector array 210 is located opposite the radiation source 208 across the first field of view 104. The radiation sensitive detector array 210 detects x-ray radiation traversing the first field of view 104 and generates a first signal indicative thereof. A CT reconstructor 212 processes the signal and reconstructs CT images.

The second modality $102_2$ is slideably affixed to the examination room floor 204, for example, via a slide mechanism 214, which may include a slide, ball, and/or other bearing and/or other type of mechanism such as wheels, etc. The second modality $102_2$ translates on the slide mechanism 214 along the scan axis 110 between at least the first location position 114 at which the second field of view 112 aligns with a second examination zone 116 (FIG. 2) and the location 118 at which the second field of view 112 is outside of the second examination zone 116 at the home or park location (FIG. 3). The second modality $102_2$ can be moved via a motor and drive system or the like through the console 130 and/or controls (not visible) located at the second modality $102_2$.

A gamma radiation sensitive detector ring 216 includes a plurality of analog detectors (e.g., scintillators with photomultiplier tubes, photodiodes, etc.) arranged around the field of view 112. The detector ring 216 detects gamma radiation emitted from inside the field of view 112 (e.g., from inside a patient positioned in the field of view 112) and generates a single indicative thereof such as list mode data, or a list of detected annihilation events, including a detection time, a position and orientation of the corresponding line-of-response (LOR), etc. Where the second modality $102_2$ is configured with time-of-flight (TOF) capabilities, the data may also include an estimate of the position of the annihilation along each LOR. An analog PET reconstructor 218 reconstructs the PET data and generates first PET images.

The third modality $102_N$ is slideably affixed to a support 220. In the illustrated embodiment, the support 220 supports or suspends the third modality $102_N$ from above the imaging apparatus 100. As shown in greater detail in FIGS. 4-6, the support 220 can include members that mount to the examination room floor 204, or, alternatively, the support 220 mounts to the examination room ceiling, an examination room wall, and/or other component. The third modality $102_N$ translates along the support 220 in a direction traverse to the scan axis 110 between the second location 114 at which the second field of view 112 aligns with the second examination zone 116 (FIG. 3) and home or park location 122 (FIG. 2, but not visible). In one configuration, the third modality $102_N$ is configured to be freely moved, manually by an operator, for example, pushing or pulling the second modality $102_2$ after releasing a locking or braking mechanism. In another embodiment, the third modality $102_N$ can be moved via a motor and drive system or the like.

A gamma radiation sensitive detector ring 224 includes a plurality of sold state detectors (e.g., Geiger-mode photodetectors, solid-state photomultipliers, silicon photomultipliers, etc.) arranged the field of view 120. The detector ring 224 detects gamma radiation emitted from inside the field of view 120 (e.g., from inside a patient positioned in the field of view 120) and generates a single indicative thereof, and a digital PET reconstructor 226 reconstructs the signal and generates second PET images. An optional alignment device 222 is located between the third modality $102_N$ and the support 220. As described in greater detail below, the alignment device 222 allows translational and/or rotational movement of the third modality $102_N$. Such movement can be used to align the field of view 120 of the third modality $102_N$ and the second examination region 116.

It is to be appreciated that the reconstructors 212, 218, and 226 may be part of different computing devices. Alternatively, at least two of the reconstructors 212, 218, and 226 are part of one computing devices and the other of the reconstructors 212, 218, and 226 is part of another computing device. In one instance, the computing device(s) includes the console 130 and/or the console 132. In another instance, the computing device(s) may be separate from the console 130 and/or the console 132. The corresponding reconstructed data from the reconstructors 212, 218, and 226 can be individually visually presented and/or visually presented as a combination such as superimposed images, subtracted images, and/or otherwise processed images, and/or filmed, conveyed over a network to an archiver, and/or otherwise utilized.

With the configuration of the apparatus 100 in FIGS. 2 and 3, i.e., the second imaging modality $102_2$ being an analog PET scanner and the third imaging modality $102_N$ being a digital PET scanner, analog and digital PET scans can be performed consecutively, one right after the other, with the apparatus 100, which may mitigate additional administration of an imaging agent, for example, which may otherwise be required due to the decay of the isotope due to the time between the two scans. Furthermore, the subject or object motion may be mitigated as the subject or object only needs to be moved enough to swap the imaging modalities in the second examination zone 116, and this may result in improved registration of the data sets and thus image quality.

Figure 4:
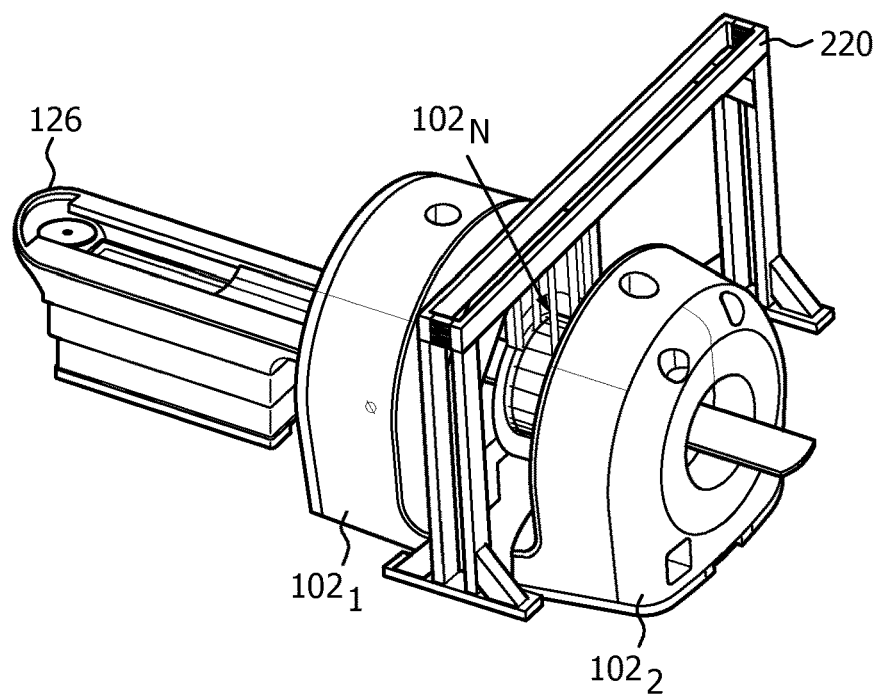
FIG. 4 illustrates an example of the imaging apparatus of FIG. 1 in which the imaging apparatus includes a stationary CT scanner, a moveable analog PET scanner, and a moveable digital PET scanner.
Figure 5:
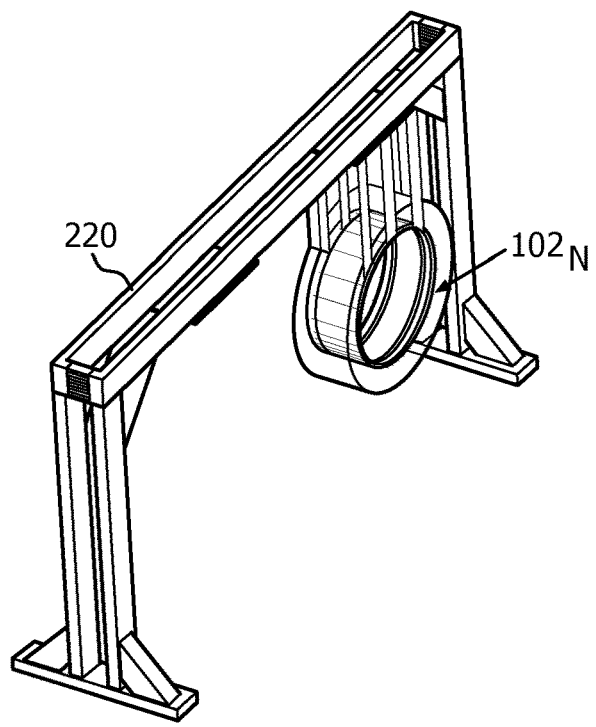
FIG. 5 illustrates a support mechanism (without the CT and analog PET and subject support) of FIG. 4 for supporting and moving the moveable digital PET scanner with the moveable digital PET scanner attached thereto.
Figure 6:
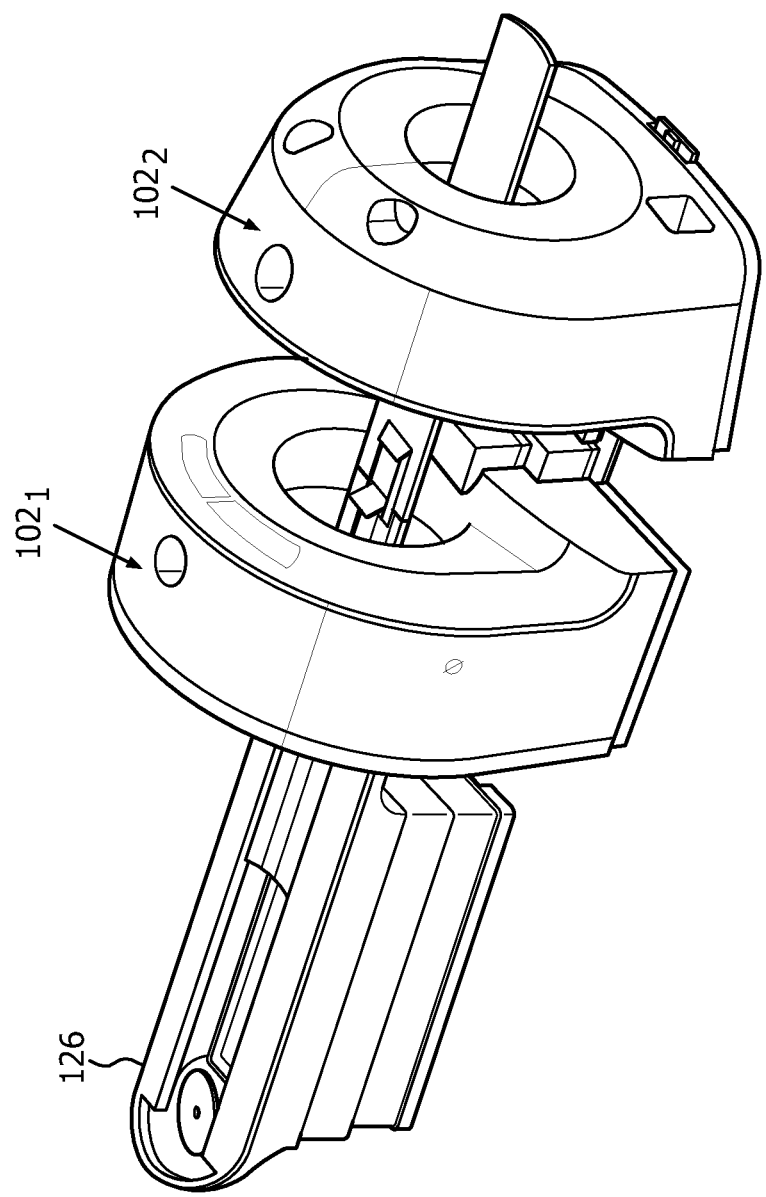
FIG. 6 illustrates the example imaging apparatus of FIG. 4 without the support mechanism and digital PET scanner.

FIGS. 4, 5 and 6 illustrate example perspective views respectively of the apparatus 100 of FIGS. 2 and 3 (FIG. 4) and the apparatus 100 of FIGS. 2 and 3 with the second imaging modality $102_N$ (FIG. 5) separated from the imaging modalities $102_1$ and $102_2$ (FIG. 6). As discussed herein, the apparatus 100 can be installed as shown in FIG. 4, or as shown in FIG. 6, with removal and/or incorporation of the third imaging modality $102_N$ as desired.

With the configuration shown in FIG. 4, the third imaging modality $102_N$ can be removed from the apparatus without affecting the other two modalities. For instance, the support 220 can be unmounted from the examination room floor and removed. Where the console 132 (and not the console 130) is used to control the third imaging modality $102_N$, no changes, mechanical, electrical or software, are needed for the apparatus 100 to continue operating via the console 130 with the first and second imaging modalities $102_1$ and $102_2$. The third imaging modality $102_N$ can also be incorporated back into the apparatus 100. In one instance, this results in adding the same modality back to the apparatus or a different modality.

With the configuration shown in FIG. 6, the third imaging modality $102_N$ can be added to the apparatus without affecting the other two modalities. For instance, the support 220 can be mounted to the examination room floor as shown in FIG. 4. Where the console 132 (and not the console 130) is used to control the third imaging modality $102_N$, no changes, mechanical, electrical or software, are needed for the apparatus 100 to continue operating via the console 130 with the first and second imaging modalities $102_1$ and $102_2$, but the apparatus 100 now also includes the functionality provided by the third imaging modality $102_N$.

In another instance, the first or the second modality is an MR scanner.

In another instance, the first or the second modality is a SPECT scanner.

FIGS. 7A, 7B, 7C and 7D illustrate an example of the alignment device 222.

Figure 7A:
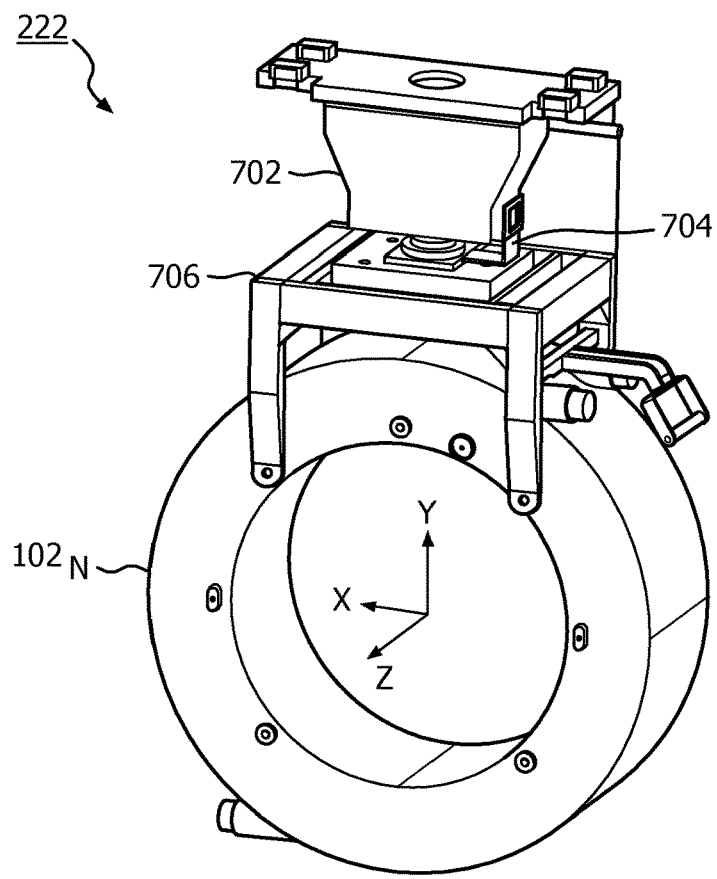
FIGS. 7A, 7B, 7C and 7D illustrate an example of the alignment device.

Initially refereeing to FIG. 7A, the alignment device 222 includes a block 702, a 3D alignment unit 704 and a gantry mounting frame 706. The block 702 is mechanically connected to the 3D alignment unit 704 and mechanically and slidably fastens to the support 220 (FIG. 2). The gantry mounting frame 706 is mechanically connected to the 3D alignment unit 704 and supports the imaging modality $102_N$. The 3D alignment unit 704 provides at least fine adjustment of the position and the orientation of the imaging modality $102_N$ with respect to the iso-center of the imaging modality $102_1$ (FIGS. 1, 2, 4 and 6), as well as a stiff connection and/or angular variation in rotation around the X and Z axes and linear alignment along the Y axis.

Figure 7B:
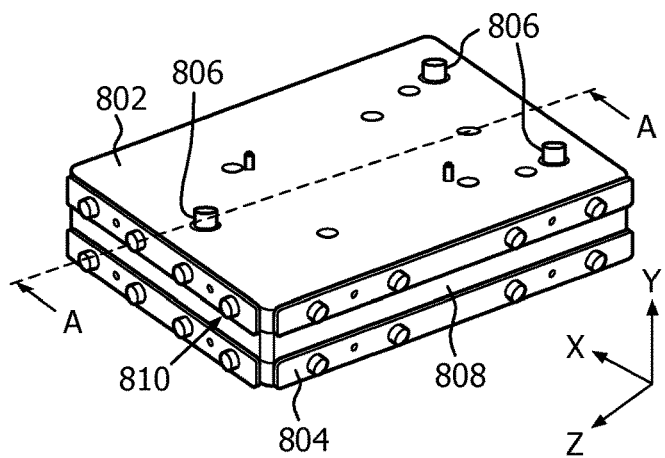
Figure 7C:
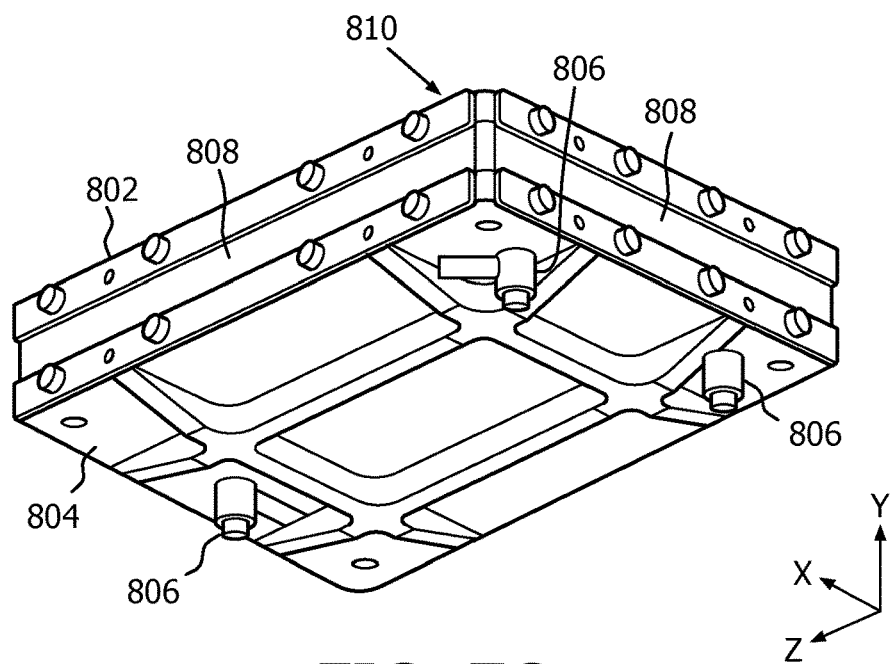

FIGS. 7B and 7C show a more detailed view of the 3D alignment unit 704. Generally, alignment is achieved by adjusting the tilt angle and the distance between a top plate 802 and a bottom plate 804 with three alignment screw-nut pairs 806. Spherical washer pairs are used at each bolt/plate interface to compensate for the changing tilt angle between both plates. The stiffness in all 6 degrees of freedom between the top and bottom plates 802 and 804 is realized by leafsprings 808, fastened firmly to the four sides of the plates 802 and 804. Screws 810 at the top side of the leafsprings 808 are loosened during the adjustment procedure and fastened after it is completed. The leafsprings 808 are provided with vertically oriented slots (not visible) for allowing vertical position change at the interfaces of the screws 810.

Figure 7D:
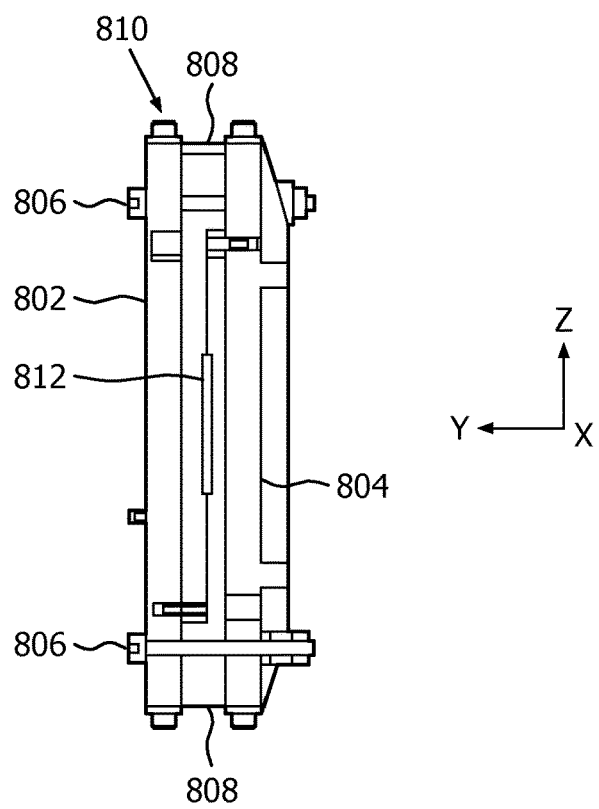

FIG. 7D shows a cross-sectional view along line A-A of FIG. 7B. A spring-plate 812, fastened between and parallel to the top and bottom alignment plates 802 and 804, removes the X, Z and the rotation around Y axis degress of freedom between them, which may avoid unwanted shift during alignment. The vertical screws 806, loaded by the imaging modality detector gravity force, provide support in the other three degrees of freedom (same as the alignment directions of this unit). During normal operation the detector weight is carried mainly by the leafsprings 808 but the vertical screws 806 carry a part of it too.

Variations are contemplated.

In FIGS. 1-6, one of the modalities translates along the scan axis 110 and one of the modalities translate along an axis transverse to the scan axis 110. In FIG. 8, two or more (three shown—$102_2$, $102_1$ and $102_N$) imaging modalities translate along the axis transverse to the scan axis 110. In this variation, the imaging modalities $102_2$, $102_1$ and $102_N$ translate along a track 902 affixed to the examination room floor, the examination room ceiling, the examination room wall, and/or other component.

In one instance, the track 902 is similar to the slide mechanism 214 shown in FIGS. 2 and 3 mounted to the floor. In another instance, the imaging modalities $102_2$, $102_1$ and $102_N$ translate along the overhead support 220 suspended above the floor as shown in FIGS. 2-6. In yet another instance, a combination of the support 220 and the slide mechanism 902 is used. For example, both mechanisms can be used with an imaging modality or one can be used with one imaging modality the other is used with another.

FIG. 9 illustrates a variation of FIG. 8 in which the imaging modalities $102_2$, $102_1$ and $102_N$ are located between the subject support 124 and the stationary first imaging modality 102₁. The imaging modalities 102₂, and 102₁ and 102ₙ are shown outside of the examination zone share thereby, and the subject support 124 is extended to the examination zone of the stationary first imaging modality 102₁.

In FIG. 10, the imaging modalities 102₂ and 102ₙ are located on a turntable 1002 like mechanism and are alternatively positioned for scanning by rotating the turntable 1002 until the desired imaging modality is aligned along the scan axis 110. In FIG. 10, the imaging modalities are arranged in a row along the scan axis 110.

FIG. 11 is similar to FIG. 10 except that there are at least three imaging modalities 102₂, 102₁, and 102ₙ located on the turntable 1002, and the at least three imaging modalities 102₂, 102₁, and 102ₙ are arranged angular offset from each other.

In another variation, the stationary first imaging modality 102₁ is omitted from the apparatus 100, and the apparatus 100 only includes moveable imaging modalities.

In yet another variation, the first imaging modality 102₁ is also moveable.

FIG. 12 illustrates an example method for scanning a subject or object with multiple imaging modalities of a single imaging apparatus.

It is to be appreciated that the ordering of the acts in the methods described herein is not limiting. As such, other orderings are contemplated herein. In addition, one or more acts may be omitted and/or one or more additional acts may be included.

At 1202, a first imaging modality of the imaging apparatus is moved into an examination zone of the imaging apparatus.

At 1204, a subject support moves a subject or object into the examination zone.

At 1206, the subject or object is scanned with the first imaging modality.

At 1208, the subject support moves the subject or object out of the examination zone.

At 1210, the first imaging modality is moved out of the examination zone.

At 1212, a second imaging modality of the imaging apparatus is moved to the examination zone.

At 1214, the subject support moves the subject or object into the examination zone.

At 1216, the subject or object is scanned with the second imaging modality.

At 1218, the subject support moves the subject or object out of the examination zone.

At 1220, the second imaging modality is moved out of the examination zone.

Optionally, the subject or object can also be scanned with another imaging modality of the imaging apparatus at another examination zone of the imaging apparatus.

Acts 1202-1220 can be repeated one or more times for one or more subject or objects.

FIG. 13 illustrates another example method.

It is to be appreciated that the ordering of the acts in the methods described herein is not limiting. As such, other orderings are contemplated herein. In addition, one or more acts may be omitted and/or one or more additional acts may be included.

At 1302, first, second and third imaging modalities of an imaging system are pre-aligned with scanning zones for scanning an object or subject, wherein the first imaging modality is moveable between the scanning zone and a location outside of the scanning zone.

At 1304, for a first scan, the first imaging modality is moved to the location outside of the scanning zone. For example, the first scan may be a clinical scan, where the first imaging modality includes a non-clinical (or research or prototype) scanner.

At 1306, for a second scan, the first imaging modality is moved to the scanning zone. For example, the second scan may be a non-clinical or research scan, where the first imaging modality is a non-clinical (or research or prototype) scanner.

At 1308, the first imaging modality is removed from the imaging system and replaced with a fourth imaging modality, which includes a non-clinical scanner and which is aligned with the scanning zones.

At 1310, for a third scan, the fourth imaging modality is moved to the location outside of the scanning zone. For example, the fourth scan may be a clinical scan.

At 1312, for a fourth scan, the fourth imaging modality is moved to the scanning zone. For example, the fourth scan may be a non-clinical or research scan.

At 1314, the fourth imaging modality is removed from the imaging system and replaced with a fifth imaging modality, which includes a clinical scanner and which is aligned with the scanning zones.

At 1316, for a fifth scan, the fifth imaging modality is moved to the location outside of the scanning zone.

At 1318, for a sixth scan, the fifth imaging modality is moved to the scanning zone.

The above may be implemented by way of computer readable instructions, encoded or embedded on computer readable storage medium, which, when executed by a computer processor(s), cause the processor(s) to carry out the described acts. Additionally or alternatively, at least one of the computer readable instructions is carried by a signal, carrier wave or other transitory medium.

The invention has been described with reference to the preferred embodiments. Modifications and alterations may occur to others upon reading and understanding the preceding detailed description. It is intended that the invention be construed as including all such modifications and alterations insofar as they come within the scope of the appended claims or the equivalents thereof.

The invention claimed is:

1. An imaging apparatus, comprising:
a first imaging modality;
a second imaging modality, wherein the first and second imaging modalities are in alignment with scanning zones for scanning an object or subject;
a third imaging modality which is selectively moveable between a first location in which the third imaging modality is in alignment with the scanning zones for scanning the object or subject and a second location in which the third imaging modality is outside of alignment with the scanning zones; and
an alignment unit that supports the third imaging modality, wherein the alignment unit provides adjustment of at least of a position or orientation of third imaging modality with respect to the scanning zones and provides angular variation in rotation around X and Z axes.

2. The imaging apparatus of claim 1, wherein at least two of the first, second and third modalities are different imaging modalities.

3. The imaging apparatus of claim 1, wherein at least two of the first, second and third modalities are a same type of imaging modality.

4. The imaging apparatus of claim 3, wherein the third imaging modality is positioned at the second location when the imaging apparatus is used for clinical scanning.

5. The imaging apparatus of claim 3, wherein the third imaging modality is positioned at the first location when the imaging apparatus is used for non-clinical scanning.

6. The imaging apparatus of claim 1, wherein the third imaging modality is removably affixed to the imaging apparatus and is interchangeable with at least one other imaging modality.

7. The imaging apparatus of claim 1, further comprising:
a support that supports the third imaging modality suspended above an examination room floor, wherein the third imaging modality is slideably coupled to the support and slides via the support to the first location.

8. The imaging apparatus of claim 1, further comprising:
a slide mechanism affixed to at least one of an examination room floor, an examination room ceiling, an examination room wall, or other component, wherein the third imaging modality is slideably coupled to the slide mechanism and slides via the slide mechanism to the first location.

9. The imaging apparatus of claim 1, wherein the alignment unit provides linear alignment along an Y axis.

10. A method, comprising:
moving a first imaging modality alternately between a first location in which the first imaging modality is in alignment with scanning zones of second and third imaging modalities and a second location in which the first imaging modality is outside of alignment with the scanning zones; and
moving the third imaging modality to provide angular variation in rotation around X and Z axes.

11. The method of claim 10, wherein at least two of the first, second and third modalities are different imaging modalities.

12. The method of claim 10, wherein at least two of the first, second and third modalities are a same type of imaging modality.

13. The method of claim 12, further comprising:
positioning the first imaging modality at the second location when the imaging apparatus is used for clinical scanning.

14. The method of claim 12, further comprising:
positioning the first imaging modality at the first location when the imaging apparatus is used for non-clinical scanning.

15. The method apparatus of claim 10, wherein the first imaging modality is removably affixed to the imaging apparatus and is interchangeable with at least one other imaging modality.

* * * * *